United States Patent [19]

Hartog et al.

[11] Patent Number: 4,538,462
[45] Date of Patent: Sep. 3, 1985

[54] ADHESIVE BOND INTEGRITY EVALUATION METHOD

[75] Inventors: Jan J. Hartog; Jack L. Bellin; Gilbert C. Knollman; Arthur D. Jonath, all of Palo Alto, Calif.

[73] Assignee: Lockheed Corporation, Burbank, Calif.

[21] Appl. No.: 560,639

[22] Filed: Dec. 12, 1983

[51] Int. Cl.³ ............................................. G01N 29/00
[52] U.S. Cl. ....................................... 73/577; 73/587; 73/801; 73/810
[58] Field of Search .................. 73/577, 582, 642, 810, 73/834, 851, 587, 801

[56] References Cited
U.S. PATENT DOCUMENTS 3,529,465 9/1970 Kleesattel et al. ..................... 73/577
3,911,734 10/1975 Mehdizadeh ........................... 73/577

Primary Examiner—Howard A. Birmiel
Attorney, Agent, or Firm—Louis L. Dachs

[57] ABSTRACT

The invention is a method of determining whether an adhesively bonded joint between two structural elements meets established strength requirements. The method comprises the following steps: (1) Determining by test the levels of acoustic energy to be directed and/or focused by a transducer 12 on a minute area of the adhesively bonded joint 14 and further the application times thereof. The combinations of directed and/or focused acoustic energy and application time are selected to macroscopically stress and/or strain-to-failure the minute area of the adhesively bonded joints having minimum acceptable bond strength or less; (2) Directing and/or focusing by means of a transducer 12 acoustic energy on the minute area of the adhesively bonded joint to be tested and steadily increasing the directed and/or focused acoustic energy/time up to the selected combination which would macroscopically stress and/or strain-to-failure the minute area of the adhesively bonded joint 14 were it of less than minimum acceptable bond strength, and (3) Monitoring by means of one or more focused and/or unfocused acoustic receiver 24 the interaction of the directed and/or focused acoustic energy with the minute area of the adhesively bonded joint 14 and/or the acoustic emission therefrom, a sudden change in the monitored acoustic interaction and/or emission, while the directed and/or focused acoustic energy/time is being steadily increased, indicating bond unacceptability.

11 Claims, 6 Drawing Figures

ADHESIVE BOND INTEGRITY EVALUATION METHOD

The U.S. Government has a paid-up license in this invention and the right in limited circumstances to require the patent owner to license others on reasonable terms as provided for by the terms of Contract No. N00030-79-C-0068 awarded by the U.S. Navy.

TECHNICAL FIELD

The invention relates to the field of inspection devices, and in particular ultrasonic inspection devices for determining an acceptable strength level of adhesively bonded joints.

BACKGROUND ART

Structures using adhesively bonded joints, whether metal-to-metal, metal-to-composite, or composite-to-composite have been used in many design fields, in particular aircraft. The use of adhesives has many advantages, in particular the elimination of fastener holes which improves fatigue life and provides a reduction in fabrication costs.

Many factors affect the quality of adhesively bonded joints, but a primary factor is the surface condition of the parts to be joined. Unfortunately, proper surface condition cannot be easily determined by physical inspection. Thus, one of the major problems with adhesively bonded joints is the determination of whether the bond has an acceptable strength level.

One of the typical ways of determining the quality of the bond is to destructively test test-coupons fabricated along with the part using the same batch of adhesive. Destructive tests are also made on randomly selected production parts. Thus, evaluation of the bonded joints is based on statistical and process control variables. While this procedure is quite satisfactory in many applications, destructive tests can become quite costly, particularly if the part is a large assembly such as a 20×40 foot fuselage section of an aircraft.

There are, however, numerous nondestructive inspection techniques that can be used to detect the quality of bonds. For example, the well known ultrasonic inspection techniques wherein a transducer is placed on the surface of the part and the reflected sound wave is monitored. This technique is quite satisfactory for determining the existence of debonds (areas where bonding between the two parts has not occurred). Typical examples of this technique can be found in the following patents: U.S. Pat. No. 2,431,233, "Supersonic Measuring Means," by W. S. Erwin; U.S. Pat. No. 2,499,459, "Resonance Device for Inspecting Materials," by B. Carlin; U.S. Pat. No. 2,522,924, "Supersonic Inspection Apparatus," by N. G. Branson; U.S. Pat. No. 2,549,891, "Supersonic Testing," by B. Carlin; U.S. Pat. No. 2,661,714, "Ultrasonic Gauge," by I. A. Greenwood, Jr., et al; U.S. Pat. No. 2,705,422, "Ultrasonic Inspection Device," by E. A. Henry.

All the prior references cited above are very limited in that they can only accurately locate a flaw in the material, or determine the thickness of the material and debonds. They are not useful for or adapted to determining if the joint can meet minimum acceptable strength levels.

There have, of course, been ultrasonic inspection techniques and equipment developed to test the strength of adhesively bonded joints. For example, U.S. Pat. No. 3,014,364, "Means for Testing Bond Strength," by R. C. Crooks. This process consists of generating an ultrasonic continuous wave signal of substantially constant average energy level for driving a piezoelectric transducer arranged in parallel with an energy measuring circuit. The transducer, when seated on the part to be inspected, exhibits a characteristic impedance which is proportional to the magnitude of restraint against the vibration of the transducer. This impedance level, which is affected among other things by the bond properties of the part under inspection, controls the energy level flowing in the energy measuring circuit. An indication of bond quality may be obtained relative to that exhibited by a similar part of known bond quality.

Here the problem is that this method does not establish bond strength, i.e., a minute area of the joint is not stressed to a minimum acceptable level but rather the effect of the bond on the impedance of the transducer is measured. Additionally, the transducer must make direct contact with the part. Another example of this type of technique can be found in U.S. Pat. No. 2,851,876, "Ultrasonic Apparatus for the Non-destructive Evaluation of Structural Bonds," by J. S. Arnold.

Other patents of interest include U.S. Pat. No. 2,345,679, "Method of Testing Pneumatic Tire Casings," by H. J. Linse; U.S. Pat. No. 2,431,234, "Automatic Sonic Measuring Means," by G. M. Rassweiler, et al; U.S. Pat. No. 2,439,131, "Resonance Inspection Method," by F. A. Firestone; U.S. Pat. No. 2,488,290, "Piezoelectric Crystal Holder," by H. B. Hansell; U.S. Pat. No. 2,494,433, "Transducer Holder," by W. S. Erwin; U.S. Pat. No. 2,618,968, "Supersonic Testing Apparatus," by R. A. McConnell.

Therefore, it is a primary object of this invention to provide a method for determining whether an adhesively bonded joint can meet specified strength requirements.

It is another object of the subject invention to provide a method for determining whether a localized area of an adhesively bonded joint meets minimum specified strength levels by stressing and/or straining the localized area to the minimum specified strength level.

It is a further object of the subject invention to provide a method for determining whether an adhesively bonded joint meets minimum strength requirements by use of either contacting or noncontacting apparatus.

DISCLOSURE OF INVENTION

The invention is a method for determining whether an adhesively bonded joint between two structural elements meets established strength requirements. The method comprises the following steps.

1. Determining by test the levels of acoustic energy to be directed to and/or focused on a minute area of the adhesively bonded joint and further the application times thereof. The combinations of directed and/or focused acoustic energy and application time are selected to macroscopically stress and/or strain-to-failure the minute area of the adhesively bonded joints having minimum acceptable bond strength or less.
2. Directing and/or focusing by means of a transducer arrangement acoustic energy on a minute area of the adhesively bonded joint to be tested and steadily increasing the directed and/or focused acoustic energy/time up to the selected combination which would macroscopically stress and/or strain-to-failure the minute area of the adhesively bonded joint were it of less than minimum acceptable bond strength.

3. Monitoring by means of one or more focused and/or unfocused acoustic receivers the interaction of the directed and/or focused acoustic energy with the minute area of the adhesively bonded joint and/or the acoustic emission therefrom. A sudden change in the monitored acoustic interaction and/or emission while the directed and/or focused acoustic energy is being steadily increased is an indication of bond unacceptability.

The novel features which are believed to be characteristic of the invention both as to its organization and method of operation, together with further objects and advantages thereof, will be better understood from the following description connected with the accompanying drawings in which presently preferred embodiments of the invention are illustrated by way of examples. It is to be expressly understood, however, that the drawings are for purposes of illustration and description only, and are not intended as a definition of the limits of the invention.

BRIEF DESCRIPTION OF DRAWINGS

Illustrated in FIG. 1 is a diagram showing one form of the apparatus necessary to carry out the inspection method and which comprises a high-intensity, high-frequency transducer and an acoustic monitor assembly.

Illustrated in FIG. 2 is a diagram of an alternate apparatus necessary to carry out the method wherein the high-intensity, high-frequency ultrasonic transducer receives its own reflected or backscattered signal.

Figure 3:
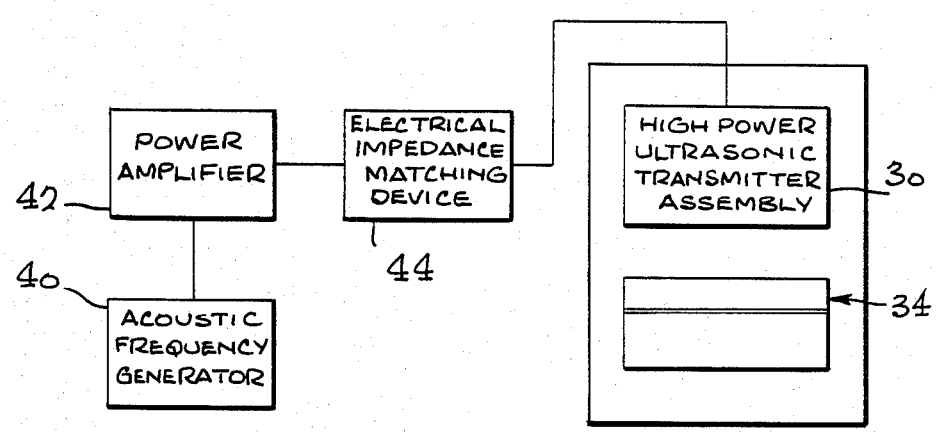

Illustrated in FIG. 3 is a block diagram of the electronic components necessary to drive the high-intensity, high-frequency transducer.

Figure 1:
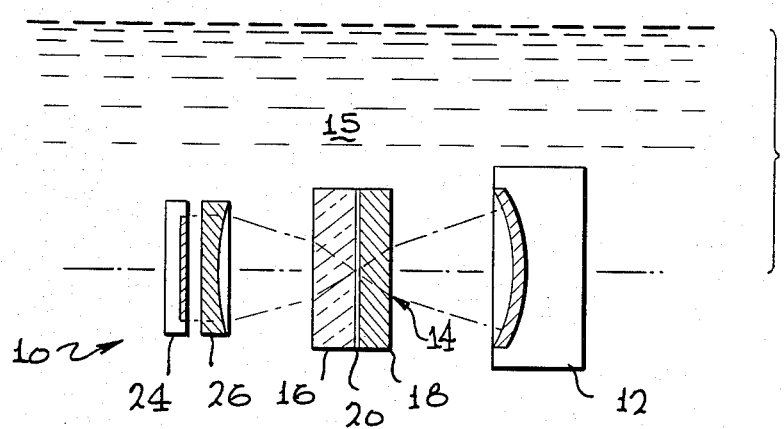
Figure 4:
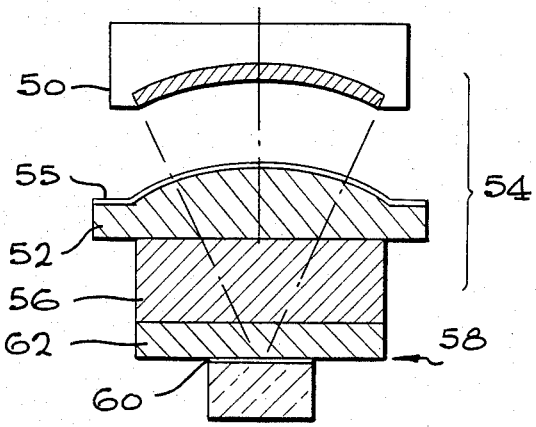

Illustrated in FIG. 4 is apparatus similar to that illustrated in FIG. 1 wherein an acoustic concentrator is used to aid in intensifying the high-frequency acoustic energy.

Figure 5:
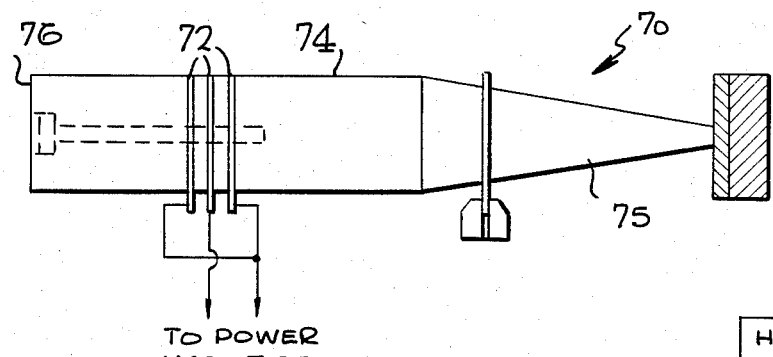

Illustrated in FIG. 5 is a diagram of a high-intensity, low-frequency transducer system which also can be used to carry out the method.

Figure 6:
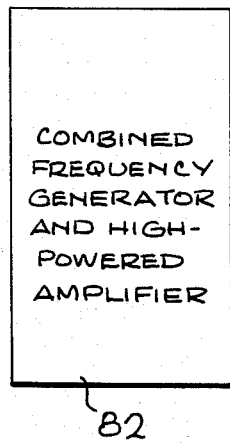

Illustrated in FIG. 6 is a schematic diagram of the electronic components necessary to drive the high-intensity, low-frequency transducer system shown in FIG. 5.

BEST MODE FOR CARRYING OUT THE INVENTION

Illustrated in FIG. 1 is the apparatus, generally designated by numeral 10, which comprises a high-intensity, high-frequency sound transducer 12, for example, a piezoelectric transducer. Such high-powered sound transducers can be purchased commercially. They are available in various sizes and focal lengths. The choice of size and focal length depends, in any given application, on the intensity level required and the size of the bonded pieces through which the acoustic energy must be directed and/or focused. In practice, such bowl-shaped acoustic energy transducers are mounted in an appropriate fixture.

The adhesively bonded structure generally indicated by numeral 14 comprises structural elements 16 and 18 having an adhesive bondline 20. On the opposite side of the structure 14 is an acoustic receiver generally designated by numeral 24. An acoustic lens 26 may be used with the receiver 24 to focus it at the minute region of acoustic energy interaction with the adhesive. Alternatively, the acoustic receiver may be a bowl-shaped transducer. The acoustic receiver is used either to receive the sound transmitted through the bondline, or as a generator of its own soundwave and detector of its signal reflected or backscattered from the bondline region being monitored.

In the example illustrated, the system including the structure 14 are placed in a fluid such as water or oil, designated by numeral 15, the fluid acting as a coupling agent for the acoustic energy. The positioning of the transducer 12 is critical in that it is necessary that the acoustic energy be focused to a minute area on the adhesive bondline 20. The positioning of the transducer 12 and receiver 24 are determined experimentally. The transducer 12 and receiver 24 can be mechanically coupled together and scanned for rapid interrogation of any and all points along the bondline. Note that it is possible to place the receiver on the same side as the transducer.

The determination of the levels of high-intensity acoustic energy and times the acoustic energy are to be applied must also be made experimentally. This is typically accomplished by preparing a number of test specimens with varying bond strengths, i.e., properly prepared test specimens having the minimum or more strength necessary, and specimens with unacceptable bond strength. Since a primary factor in determining bond strength is the surface condition of parts to be bonded, degradation of the surfaces can provide the necessary decreases in bond strength.

A portion of each of the above groups would be destructively tested by conventional methods to insure that the proper strength levels have been achieved. Thereafter, each of the remaining specimens would be subjected to steadily increasing acoustic energy for a period of time, or to fixed acoustic energy for an increasing period of time, until a level of acoustic energy and a time value are obtained which would debond the part. These acoustic energy/time values would then correspond directly to adhesive bond strengths. In testing an actual part, the applied acoustic energy/time is steadily increased up to that corresponding to the minimum acceptable bond strength. During this process, any sudden change in the monitored interaction would indicate unacceptable bond strength.

The changes that the acoustic receiver may sense include, but are not limited to, changes in intensity, frequency, spectral content or acoustic emissions. Any or all of these can be used as an indication of unacceptable bond strength.

Figure 2:
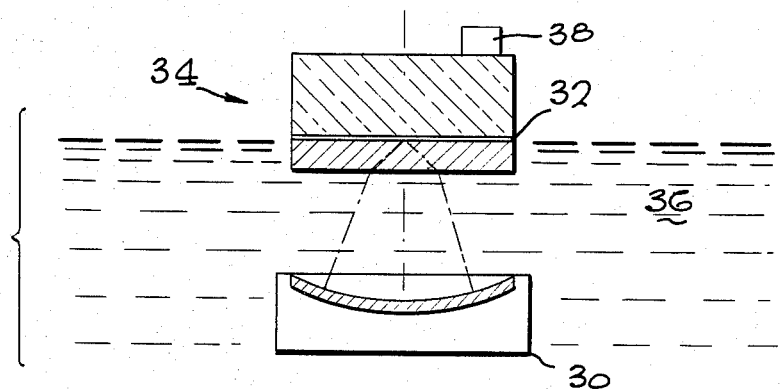

Illustrated in FIG. 2 is a diagram of an alternate embodiment. An ultrasonic transducer 30 is positioned to focus acoustic energy at the bondline 32 of an adhesively bonded structure 34. The transducer 30 is adapted to receive its own acoustic energy which is reflected or backscattered from the region of the bondline 32 undergoing interrogation. A second transducer can be used as well which would receive the backscattered signal in a pitch-catch mode. Again, a coupling medium, such as water, designated by numeral 36 is used. In addition, an acoustic transducer 38 may be used to monitor the interaction of the high-intensity sound with the adhesive bond.

Illustrated in FIG. 3 is a block diagram of the circuit required to supply the necessary signal to the transducer 12 or 30. An acoustic frequency generator 40 is coupled directly to a power amplifier 42 which in turn is coupled to an electrical impedance matching device 44. The impedance matching device 44 is coupled to the transducer 12 or 30. All of these devices are commercially available.

Illustrated in FIG. 4 is another embodiment of the invention wherein an acoustic concentrator is used to help intensify the acoustic energy at the bondline. As illustrated, an acoustic transducer 50 is combined with an ultrasonic power concentrator 52 to form a transducer assembly 54. An anti-reflective coating 55 may be applied to the concentrator 52 in order to minimize acoustic reflective losses. An adapter plate 56 is coupled to the transducer assembly 54 and rests upon the adhesively bonded structure, generally designated by numeral 58. With the aid of the concentrator 52 and spacer 56, the acoustic energy can be better concentrated at the bondline 60. This occurs because the curvature of the concentrator 52 is selected so that all rays originating at the transducer 50 enter the concentrator 52 at normal incidence in order to minimize acoustic reflection losses. Both the concentrator 52 and the adapter 56 should be made of the same material as that of the structural element 62 of the bonded structure 58. This eliminates acoustic refraction at the various interfaces.

Illustrated in FIG. 5 is a diagram of a high-intensity, low-frequency transducer, while illustrated in FIG. 6 is the transducer shown with a block diagram of a suitable electronic driving circuit. Particularly referring to FIGS. 5 and 6, the high-intensity, low-frequency ultrasonic transducer generally designated by numeral 70 typically consists of several piezoceramic elements 72, a front radiating element 74 coupled to an acoustic horn 75, and a back element 76. When the front element 74 is of appropriately lower acoustic impedance and the back element 76 is of appropriately higher acoustic impedance than that of the piezoceramic elements 72, a transducer of optimum efficiency is formed. These conditions were fulfilled in the laboratory when an aluminum front element was used with a steel back element and a lead-zirconate-titanate combination was used as the piezoceramic elements 72. To properly drive the transducer 70, all that is needed is a combined frequency generator and high-power amplifier 82 coupled to an adjustable impedance matching device 84, which in turn is coupled directly to the transducer 70.

Laboratory tests have been conducted using both high-frequency and low-frequency high-intensity transducers, both of which could be adjusted to apply sufficient acoustic energy to cause debonding of adhesively bonded joints. It was also determined that the acoustic energy could be applied in a continuous manner or in a pulsing mode. The test specimens primarily consisted of aluminum plate bonded to transparent Plexiglas. The Plexiglas was selected because it allowed visual inspection of the adhesively bonded joint after undergoing testing. Based on these tests, it was inferred that if similar tests were used to determine the proper level of acoustic energy and application time thereof and their relationship to adhesive bond strength, a method would be available to determine if an adhesively bonded joint could meet minimum acceptable strength levels.

While the invention has been described with reference to particular embodiments, it should be understood that the embodiments are merely illustrative as there are numerous variations and modifications which may be made by those skilled in the art. Thus, the invention is to be construed as being limited only by the spirit and scope of the appended claims.

Industrial Applicability

The adhesive bond integrity evaluation system has application for the inspection of adhesively bonded joints.

We claim:

1. A method of determining whether adhesively bonded joints between two structural elements have acceptable strength levels comprising the steps of:
   determining by test the levels of acoustic energy to be directed to a minute area of the adhesively bonded joint and the application times of said directed acoustic energy, said combinations of directed acoustic energy and application time selected to macroscopically stress and/or strain-to-failure said minute area of the adhesively bonded joints having minimum acceptable bond strength or less;
   directing said acoustic energy on said minute area of the adhesively bonded joint and steadily increasing said directed acoustic energy/time up to the selected combination which would macroscopically stress and/or strain-to-failure said minute area of the adhesively bonded joint were it of less than minimum acceptable bond strength;
   monitoring the interaction of said directed acoustic energy with said minute area of the adhesively bonded joint and/or the acoustic emission therefrom, a sudden change in said monitored acoustic interaction and/or emission, while the said directed acoustic energy is being steadily increased, indicating bond unacceptability.

2. The method of claim 1 wherein said acoustic energy is also focused on said minute area.

3. The method as set forth in claim 1 wherein said acoustic energy is provided by a piezoelectric transducer.

4. The method as set forth in claim 3 including the step of providing a coupling agent between said transducer and the adhesively bonded structure.

5. The method as set forth in claim 4 wherein said coupling agent is a fluid selected from the group consisting of water and oil.

6. The method as set forth in claim 5 wherein said monitoring is accomplished by said transducer.

7. The method as set forth in claim 5 wherein said monitoring is accomplished by means of at least one acoustic receiver.

8. The method as set forth in claim 6 wherein said acoustic receiver is mounted on the side of the adhesively bonded joint opposite said transducer.

9. The method as set forth in claim 6 wherein said acoustic receiver is mounted on the same side as said transducer.

10. The method as set forth in claim 6 or 7 or 8 or 9 wherein said acoustic energy is pulsed.

11. The method as set forth in claim 6 or 7 or 8 or 9 wherein said acoustic energy is delivered in a continuous fashion.

* * * * *